United States Patent
Pan

(12) 
(10) Patent No.: US 6,186,943 B1
(45) Date of Patent: Feb. 13, 2001

(54) PENIS SUPPORT DEVICE

(76) Inventor: Hung-Hsin Pan, 3F-1, No. 26, Lane 143, Sec. 1, Hsin-Sheng South Road, Taipei (TW)

( * ) Notice: Under 35 U.S.C. 154(b), the term of this patent shall be extended for 0 days.

(21) Appl. No.: 09/318,968

(22) Filed: May 26, 1999

(51) Int. Cl.[7] .................................................. A61F 5/00
(52) U.S. Cl. ............................................................. 600/39
(58) Field of Search ........................................ 600/38–41

(56) References Cited

U.S. PATENT DOCUMENTS

| | | | |
|---|---|---|---|
| 764,801 | * | 7/1904 | Emerson .................................. 600/39 |
| 853,410 | * | 5/1907 | Huebner .................................. 600/39 |
| 1,462,000 | * | 7/1923 | Bennett .................................... 600/39 |
| 4,449,521 | * | 5/1984 | Panzer ..................................... 600/39 |
| 4,653,484 | * | 3/1987 | Cannon ................................... 600/39 |
| 4,672,954 | * | 6/1987 | Panzer ..................................... 600/39 |
| 5,800,340 | * | 9/1998 | Gekhter et al. ......................... 600/39 |

* cited by examiner

*Primary Examiner*—Samuel G. Gilbert
(74) *Attorney, Agent, or Firm*—Senniger, Powers, Leavitt & Roedel

(57) ABSTRACT

A sex aid device, particularly a penis support device, for improving sex is presented, which has a support member having a first end and a second end, and having a length approximately equal to the length of a penis measured from the rear end of the glans penis to the base of the penis; a first fastening member for securing the penis to the support member; and a mounting member connected to the second end of the support member.

2 Claims, 4 Drawing Sheets

PENIS SUPPORT DEVICE

FIELD OF THE INVENTION

The present invention relates to a sex aid device, particularly a penis support device, for easily improving sexual intercourse.

BACKGROUND OF THE INVENTION

One of the reasons for divorce is an inharmonious sexual relationship between couples, which is mainly because the husband suffers from partial or complete impotence and cannot satisfy the wife's sexual desire. Therefore, satisfying the wife's sexual desire is an important issue in maintaining a pleasant marriage.

In addition, during normal sexual intercourse, a woman usually needs twenty minutes to achieve orgasm and erection can only last for ten minute before ejaculation. However, after ejaculation, the penis becomes soft and cannot provide the woman a pleasant sensation from friction between the vagina and the erect penis. Therefore, when a man achieves orgasm, a woman has not been satisfied yet. It is thus necessary to have a sex aid device to keep the penis erect after ejaculation so as to aid the wife to achieve orgasm and maintain a pleasant marriage.

ROC (Taiwan) Pat. Publ. No. 233260 discloses a penis erecting device which is embedded in the human body and comprises a support 1, a securing means 2, a supporting means 3, a cylindrical member 4 and a ring 6. The securing means 2 is attached at a side of the support 1 for receiving an end of the supporting means 3, which consists of a plurality of flexible wires made of sliver. The cylindrical member 4 is slidably fitted around the supporting means 3 and a plurality of holes 5 are formed on the surface of the cylindrical member 4 to allow bodily fluids to flow therethrough such that the cylindrical member 4 can slide smoothly according to the erection of the penis. The ring 6 is disposed on the tip of the cylindrical member 4 and is used to hold the glans penis.

The major disadvantage of the above structure is that the whole device has to be embedded in the user's body by a surgical operation which is costly and dangerous. In addition, the user has to carry the device all the time even when the user does not need it.

U.S. Pat. No. 4,429,689 assigned to Yanong discloses a sex aid device for males comprising a tubular member including upper and lower supports. The tubular member extends from the base of the penis to the glans penis and the bottom support extends forward and forms a spoonlike member for receiving the bottom of the glans penis to be exposed to tactile stimulation. Two pieces of tape are further secured to the base end of the tubular member and a tape is attached at the bottom thereof to aid in attaching the device about the body of the user.

U.S. Pat. No. 4,429,689 is used for those who suffer from impotence to aid in achieving and accommodating the erection. However, the structure of the device is too complicated and is not convenient to use and clean after sexual intercourse.

SUMMARY OF THE INVENTION

It is an objective of the present invention to provide a sex aid device which can help users suffering from impotence to achieve an erection.

It is another objective of the present invention to provide a sex aid device which can keep the penis erect after ejaculation.

It is still another objective of the present invention to provide a sex aid device which is convenient to use and clean and is not costly.

It is the other objective of the present invention to provide a sex aid device which is not embedded in the human body and needs no surgical operation.

To achieve the above objectives, the sex aid device of the present invention comprises a support member in the shape of a tube or a hollow cylindrical body having a first end and a second end, and having a length approximately equal to the length of a penis measured from the rear end of the glans penis to the base of said penis; a first fastening member for securing said penis to said support member; and a mounting member connected to said second end of said support member.

The structure and objectives of the present invention will be more readily understood by those skilled in the art from the following description of a preferred embodiment taken in conjunction with the accompanying drawings.

DETAILED DESCRIPTION OF THE PREFERRED EMBODIMENT

Figure 1:
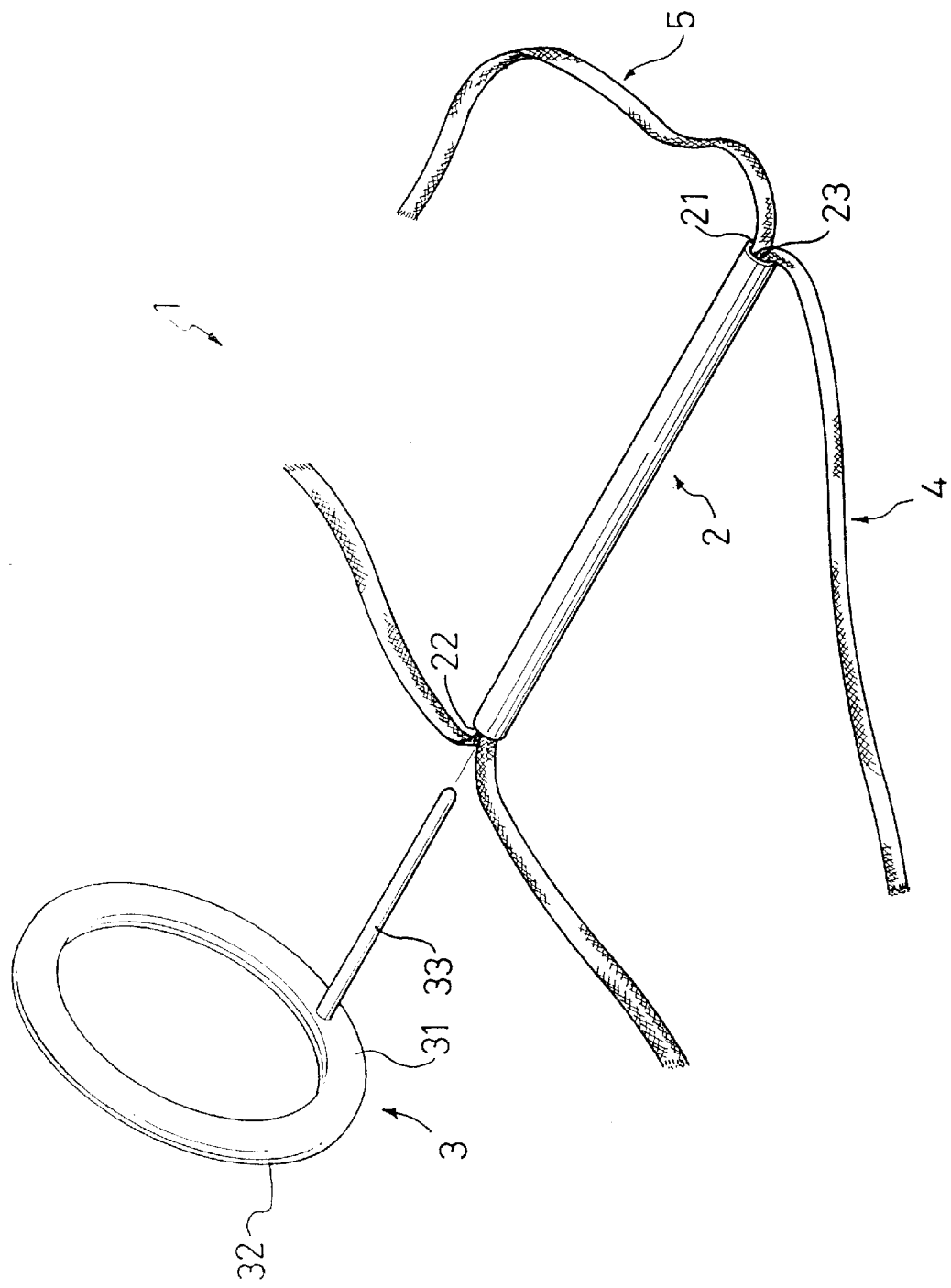
FIG. 1 is an exploded view of the sex aid device in accordance with the present invention.
Figure 3:
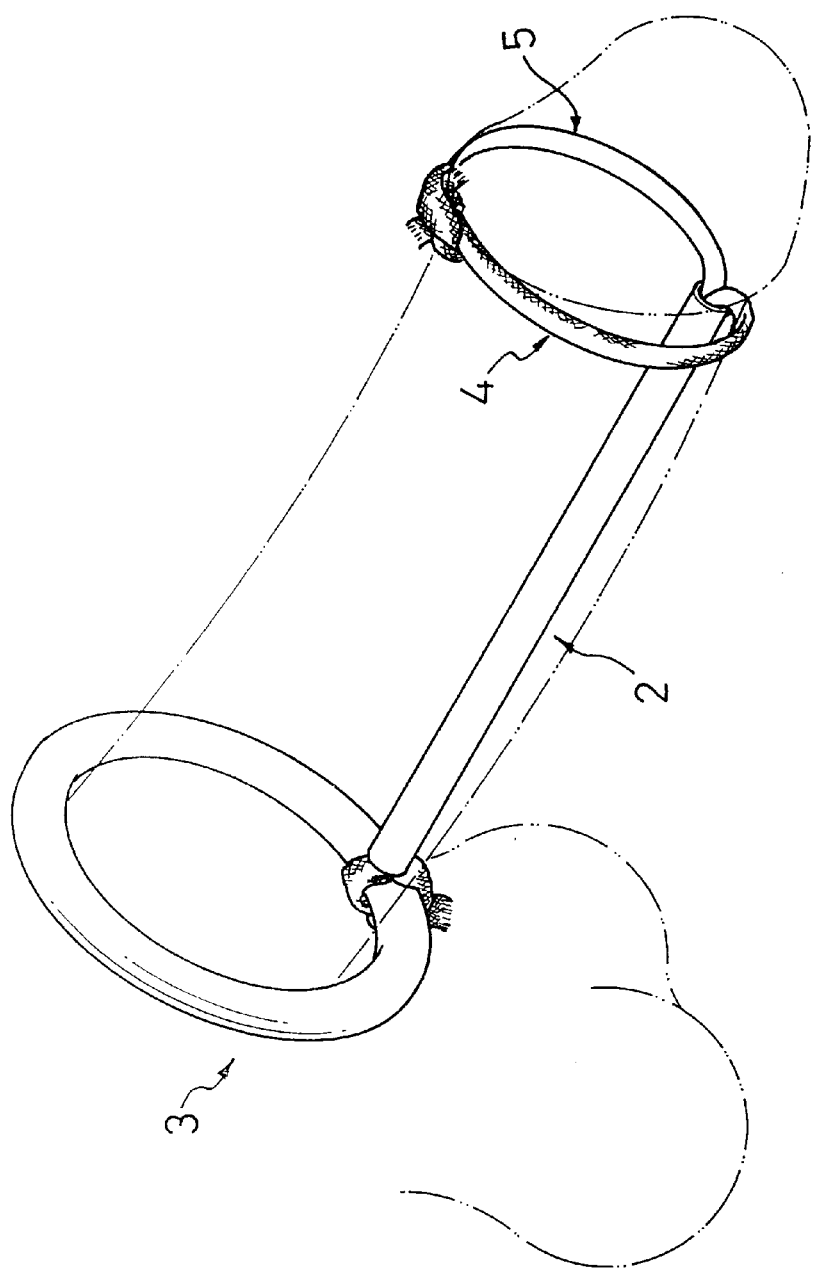
FIG. 3 is a view showing the state of use of the sex aid device in accordance with the present invention.
Figure 4:
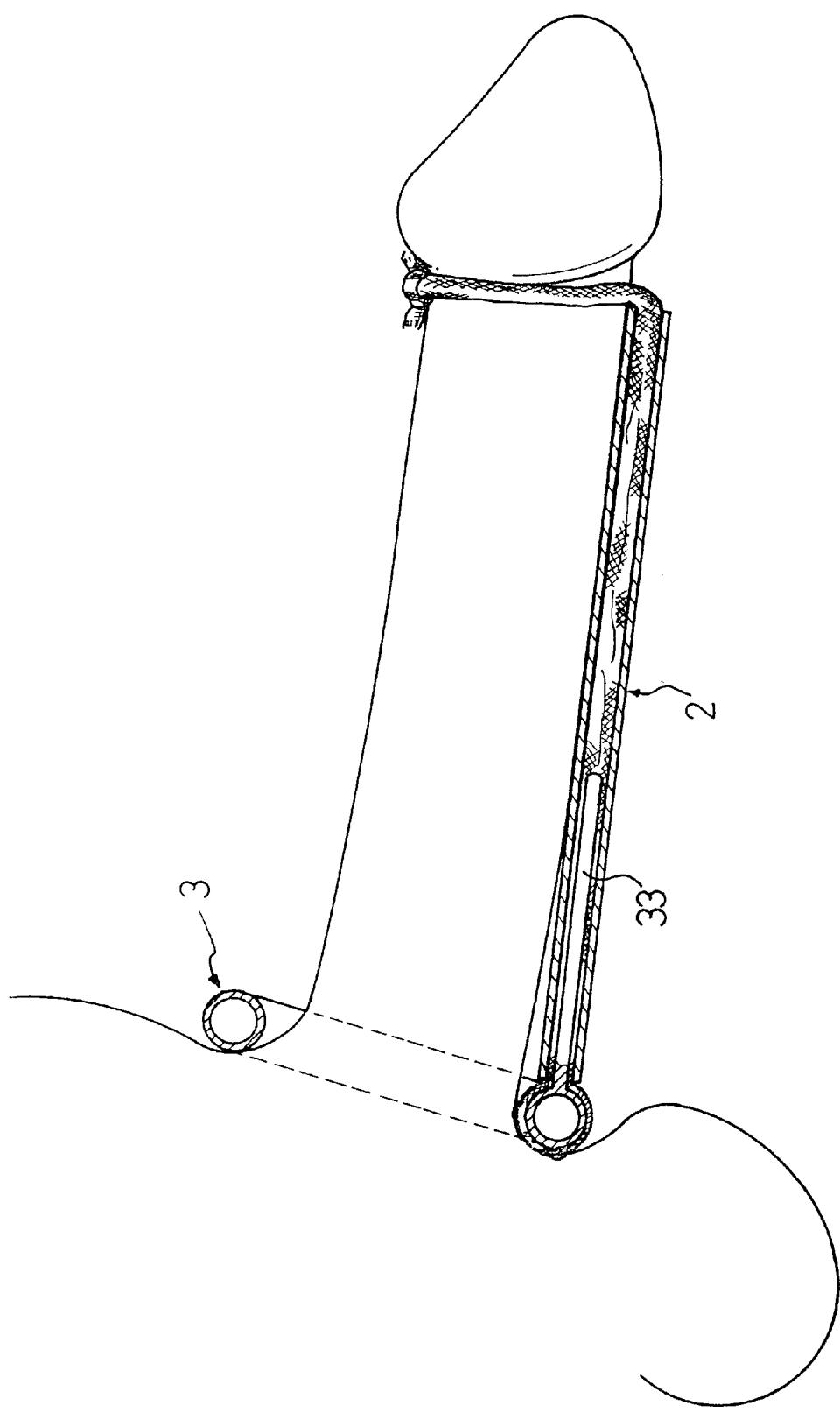
FIG. 4 is a sectional view showing the state of use of the sex aid device in accordance with the present invention.

As shown in FIG. 1, the sex aid device 1 according to the present invention comprises a support member 2, a mounting member 3, and two ropes 4, 5. The support member 2 has a first end 21 and a second end 22. The support member 2 is in the form of a tube and preferably in the shape of a hollow cylindrical body having a longitudinal hole 23 therein. The support member 2 is preferably made of stainless steel or rigid plastics and has a length approximately equal to the length of a human penis measured from the rear end of the glans penis to the base of the penis (see FIGS. 3 and 4). The support member 2 can have a length of different standards to meet different users' needs. Alternatively, the user can cut the support member 2 into an appropriate length to meet his personal needs. The ends and surface of the support member 2 are smooth.

Figure 2:
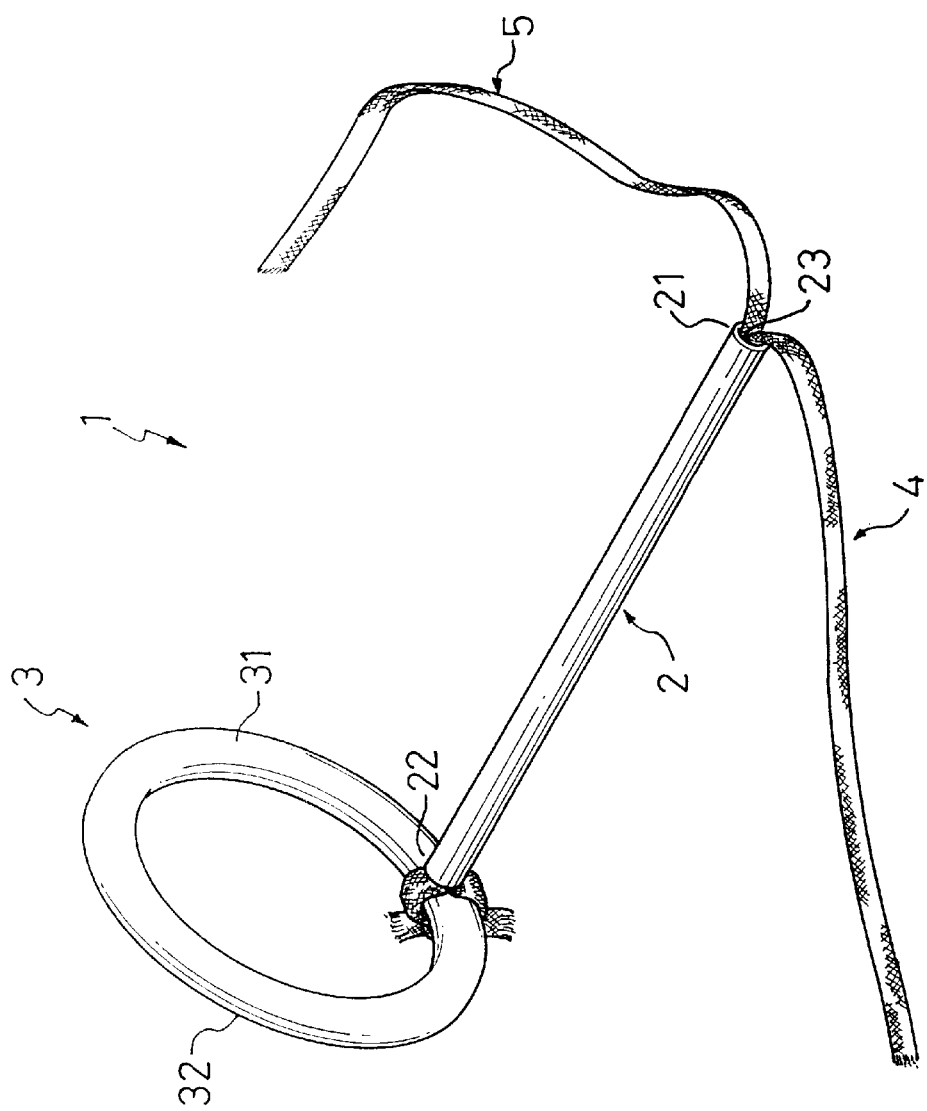
FIG. 2 is an assembly view of the sex aid device in accordance with the present invention.

The mounting member 3, or a ring 3, comprises a front face 31, a back face 32 and a bar 33 perpendicularly extending from the front face 31. The ring 3 is preferably made of stainless steel or rigid plastics and has an inner diameter larger than the diameter of the penis. The surface of the ring 3 is smooth. The bar 33 is shorter than the support member 2 and further inserts into the hole 23 of the support member 2 at the second end 22 of the support member 2 so as to connect the ring 3 to the support member 2, as shown in FIG. 2. Similarly, the ring 3 can have different sizes to meet different users' needs.

Two ropes 4, 5 go through the hole 23 of the support member 2. One end of the ropes 4, 5 emerges from the first end 21 of the support member 2 and constitutes a first fastening member. The other end thereof emerges from the second end 22 of the support member 2 and constitutes a second fastening member. The first fastening member is used to tighten the rear end of the glans penis with the support member 2 and the second fastening member is used to tighten the ring 3 with the support member 2 (see FIGS. 3 and 4). The sex aid device in accordance with the present invention is thus presented.

To use the sex aid device 1, the penis is passed through the ring 3 first and the glans penis is attached to the first end 21 of the support member 2 by the first fastening member. The back face 32 of the ring 3 is thus pressed against user's pubic bone. The user can then use his penis attached with the sex aid device 1 to proceed with sexual intercourse.

The sex aid device 1 in accordance with the present invention can be used for persons suffering from impotence from the beginning of sexual intercourse. Further, it can be used for a normal person to continue sexual intercourse by wearing it after ejaculation.

After sex, the sex aid device 1 can be easily removed from the penis by loosening the first fastening member. The sex aid device 1 can then be disassembled and cleaned.

Although the invention has been described with reference to the preferred embodiment, it will be obvious to those skilled in the art that various changes and modifications may be made without departing from the scope of the invention as recited in the claims.

What is claim is:

1. A penis support device comprising;

a support member in the shape of a hollow cylindrical body having a first end and a second end, and having a length approximately equal to the length of a penis measured from a rear end of the glans penis to the base of said penis;

a ring having a front face and a bar extending perpendicularly from said front face and being shorter than said support member, the inner diameter of said ring being larger than the diameter of said penis, said bar being inserted into said support member from said second end of said support member such that said penis can be inserted through said ring and supported by said support member; and two ropes passing through said support member, an end of each rope emerging from said first end of said support member for fastening with each other and securing the glans penis to said support member, and the other end of each rope emerging from said second end of said support member for fastening with each other and securing said ring to said support member.

2. The penis support device according to claim 1, wherein the ends and surface of said support member are smooth.

* * * * *